United States Patent [19]

Fujihira

[11] Patent Number: 4,486,272

[45] Date of Patent: Dec. 4, 1984

[54] METHOD OF ELECTROCHEMICAL MEASUREMENT UTILIZING PHOTOCHEMICAL REACTION AND APPARATUS THEREFOR

[75] Inventor: Masamichi Fujihira, Sendai, Japan

[73] Assignee: Hitachi, Ltd., Tokyo, Japan

[21] Appl. No.: 447,799

[22] Filed: Dec. 8, 1982

[30] Foreign Application Priority Data

Apr. 14, 1982 [JP] Japan .................. 57/62320

[51] Int. Cl.³ ............................ G01N 27/46
[52] U.S. Cl. .................. 204/1 T; 204/412;
422/186
[58] Field of Search .............. 204/1 T, 1 K, 412, 400,
204/158 R, 59 R, 72; 436/150; 422/186

[56] References Cited

U.S. PATENT DOCUMENTS

| | | | |
|---|---|---|---|
| 3,129,148 | 4/1964 | Steinbrecher et al. | 204/400 X |
| 3,528,778 | 9/1970 | McKaveney et al. | 436/150 X |
| 4,028,207 | 6/1977 | Faktor et al. | 204/1 T X |
| 4,233,030 | 11/1980 | Twitchett et al. | 422/186 X |

FOREIGN PATENT DOCUMENTS

WO79/00992  11/1979  PCT Int'l Appl. .................. 204/129

OTHER PUBLICATIONS

Johnson et al., Rotating Photoelectrode for Electrochemical Study of the Products of Photochem. Reactions, Analytical Chemistry, vol. 44, No. 3, 3/72, pp. 637-640.

*Primary Examiner*—G. L. Kaplan
*Assistant Examiner*—Nam X. Nguyen
*Attorney, Agent, or Firm*—Antonelli, Terry & Wands

[57] ABSTRACT

A light transmissible working electrode, an auxiliary electrode and a reference electrode are provided in an electrolytic cell having a light transmissive window. The working electrode comprises, for instance, a thin film vapor deposited on inner surface of the light transmissive window. A sample solution containing components which cause photochemical reaction is introduced into the electrolytic cell. A step-functional light emitted from a monochromatic light source is irradiated into the electrolytic cell through the light transmissive window. When light is irradiated to the light transmitting window, the light passes through the working electrode to give an energy to the sample solution to bring about photochemical reaction.

Concentrations of the components in the sample solution can be obtained from the difference between amplitude of current passing when the light is irradiated to the sample solution and amplitude when no light is irradiated. Furthermore, it also becomes possible to analyze mechanism of the photochemical reaction from the detected changes of current intensity by observing transitional phenomena of the reaction.

13 Claims, 8 Drawing Figures

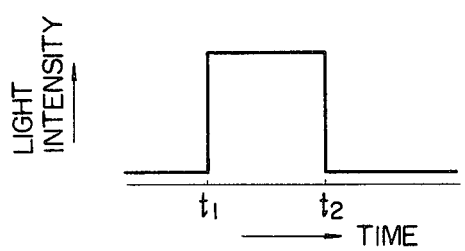
FIG. 2a
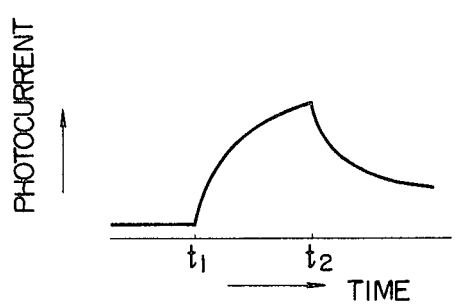
FIG. 2b
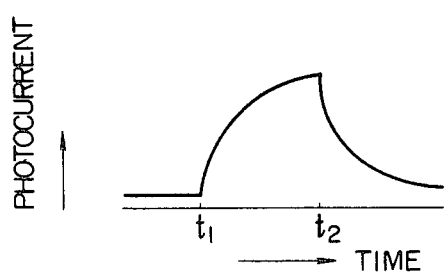
FIG. 2c
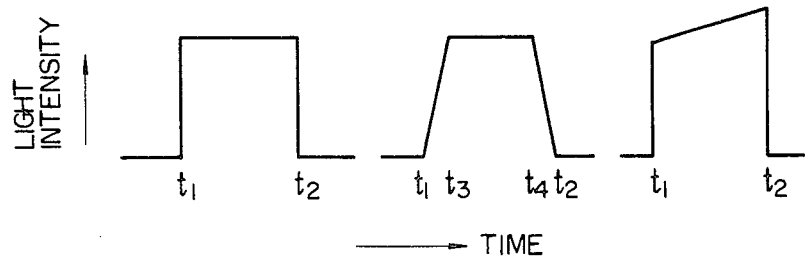

METHOD OF ELECTROCHEMICAL MEASUREMENT UTILIZING PHOTOCHEMICAL REACTION AND APPARATUS THEREFOR

BACKGROUND OF THE INVENTION

This invention relates to an electrochemical measuring method utilizing photochemical reactions and an apparatus therefor and more particularly relates to a measuring method suitable for detection of components in solutions and analysis of mechanism of photochemical reactions.

Hitherto, as methods for detecting substances contained in a solution at a high sensitivity by irradiation of light to the solution, there have been known such methods as making the detection by measuring absorption of the irradiated light per se, by measuring fluorescence emitted due to excitation with the irradiated light, by using the thermal lens effect caused by thermal expansion due to light absorption heat and by measuring light-acoustic effect, etc. These methods have the problems that they are liable to be affected by noise caused by external stray light, radiant heat or other noise because the detection is carried out with light, heat or sound.

SUMMARY OF THE INVENTION

It is therefore an object of this invention to provide a method of electrochemical measurement where a photochemical reaction can be efficiently taken place and an apparatus therefor.

A further object of this invention is to provide a method by which the photochemical reaction can be measured at high sensitivity even if sample solutions are low in light transmission and an apparatus therefor.

Another object of this invention is to provide a method according to which concentrations of substances which cause a photochemical reaction can be measured at a high accuracy and an apparatus therefor.

A still further object of this invention is to provide a method according to which transitional phenomena of the photochemical reaction can be observed and an apparatus therefor.

In this invention, an electrolytic cell with a light transmissible wall is used. A light transmissible working electrode is provided on an inner surface of the light transmissible wall. A monochromatic light which is irradiated to the electrolytic cell is transmitted through the working electrode to give an energy to the sample in the electrolytic cell. The photochemical reaction which has taken place in the electrolytic cell is detected as a change in current.

In a preferred embodiment of this invention, a working electrode and an auxiliary electrode are provided in an electrolytic cell capable of containing a sample solution and a part of the wall of the electrolytic cell is of a light transmissible material and a working electrode in the form of a film is provided on said light transmissible wall. This working electrode in the form of a film is light transmissible. The sample solution in the electrolytic cell is irradiated with a light which has been transmitted through said working electrode. The irradiated light is a monochromatic light and is irradiated to the working electrode for a predetermined period, during which the intensity of the light is kept constant over the irradiation period, that is, a step-functional light is irradiated thereto.

When this invention is applied to detection of components, concentrations of the components are calculated based on the difference between the maximum current value obtained with light irradiation and the base current value obtained with no light irradiation. When this invention is applied to an analysis of process of photochemical reactions, changes of current intensity during irradiation of light to the sample solution or attenuation of current intensity after irradiation of light are observed.

BRIEF DESCRIPTION OF THE DRAWINGS

FIG. 2(a) is a graph which shows the wave form of the irradiated light;

FIGS. 2(b) and 2(c) are graphs which show examples of the wave forms of photocurrents (photoelectrolytic current) obtained corresponding to FIG. 2(a);

FIG. 3 is a graph which comparatively explains the wave forms of irradiated light.

DETAILED DESCRIPTION OF THE PREFERRED EMBODIMENTS

Figure 1:
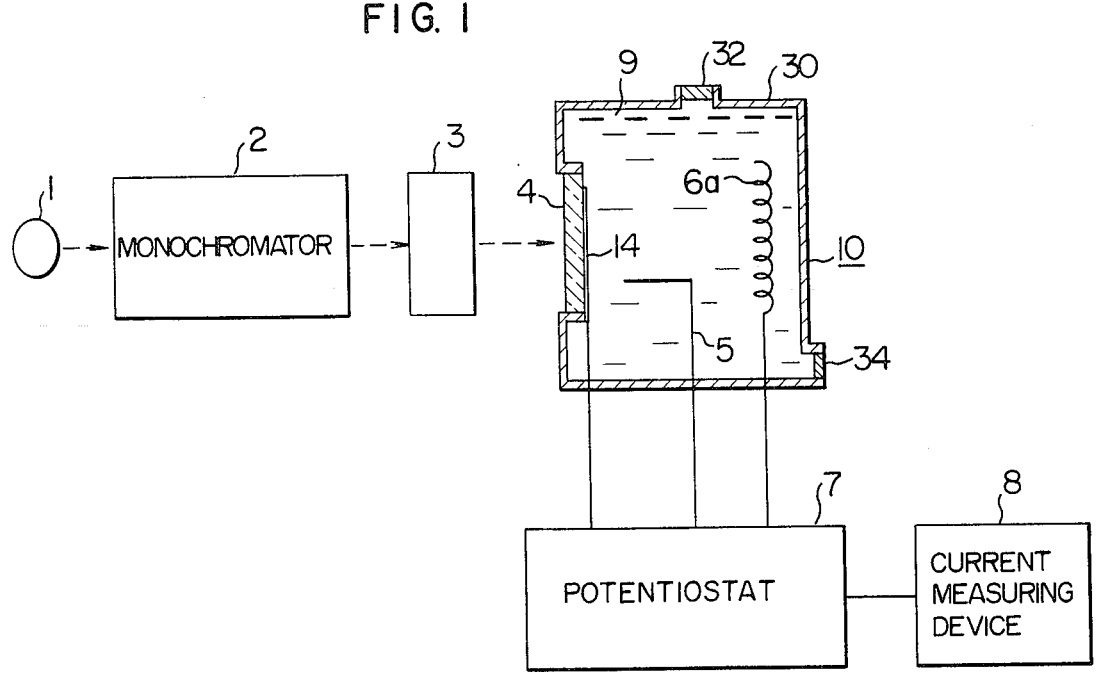
FIG. 1 is a rough block diagram which shows one embodiment of this invention.

In FIG. 1 the light from light source 1 is monochromatized by spectroscope 2 and directed to light switch 3. A mercury vapor lamp or xenon lamp may be employed as the light source 1. A laser light source may be used in place of the combination of light source 1 and the spectroscope 2. A chopper or shutter for obtaining a step-functional light as shown in FIG. 2(a) is used as the light switch 3. A rotating chopper having a blade which is usually employed for spectrophotometer may be used as the chopper. The shutter is preferably a moving member which rotates or slides a member which can intercept the light path. Both the shutter and chopper are those which can work instantaneously in another state. They work so that a step-functional or pulsed light of constant intensity as shown in FIG. 2(a) can be obtained for a given period. The light signal shown in FIG. 2(a) is obtained by opening the chopper or shutter for a given period, during which a light of constant intensity is taken out. This light signal will be called "step-functional light" hereinafter.

The step-functional light is irradiated to sample solution 9 containing substances capable of bringing about photochemical reaction in electrolytic cell 10 through working electrode 14 on light transmitting window 4. This light irradiation brings about photochemical reaction in electrolytic cell 10 and changes of electrolytic current due to this reaction are measured and recorded by photocurrent measuring device 8.

Working electrode 14, reference electrode 5 extending near the work electrode and auxiliary electrode 6a at a distance therefrom are arranged in electrolytic cell 10. The reference number 30 indicates a vessel constructed with insulating materials. To the working electrode 14 is applied a constant potential with reference to the reference electrode 5 by potentiostat 7. The working electrode 14 is provided on the light transmitting window 4. In this example, the working electrode is in the form of a film of electrically conducting material and has light transmissibility. The working electrode 14 comprises a two-layer film made by vapor depositing chromium on a quartz plate which is the light transmitting window and then vapor depositing gold thereon and thickness of this film is adjusted so that light transmittance is 25%. As the light transmissible working electrodes, a glass or quartz plate coated with tin oxide or indium oxide may also be used. Electrolytic cell 10 has inlet 32 and outlet 34 for sample solution.

In the above example, a response curve is obtained between time and photocurrent derived from photochemical reaction taking place at the interface of the electrode and the sample solution and this curve can be analyzed. Furthermore, in this example, reaction of the light-excited photoelectrochemical reaction products can be pursued and so this can be applied for elucidation of mechanism of photoelectrochemical reaction or determination of the reaction rate constants of solutions.

EXAMPLE 1

A solution containing anthraquinone (AQ) and isopropanol was contained in electrolytic cell 10 and to working electrode 14 was applied a potential at which hydroanthraquinone (AQH$_2$) produced by light irradiation is oxidized according to the reaction of the equation (1). A mercury vapor lamp of 500 W was used as light source 1.

$$AQH_2 \rightarrow AQ + 2e + 2H^+ \tag{1}$$

Irradiation of step-functional light yielded hydroanthraquinone according to the reaction of equation (2).

$$AQ + CH_3CHOHCH_3 + h\nu \rightarrow AQH_2 + (CH_3)_2CO \tag{2}$$

As a result, a photocurrent flowed through the working electrode according to the reaction of the equation (1). Contrasting the photocurrent with the irradiated step-functional light resulted in the wave form as shown in FIG. 2(b). The difference between maximum current value and base current value described in a recording device corresponds to the content of anthraquinone and hence concentration of anthraquinone is obtained from this difference.

EXAMPLE 2

0.03 mM of thionine, 1 mM of Fe$_2$(SO$_4$)$_3$ and 10 mM of FeSO$_4$ were introduced in electrolytic cell 10 as a 50 mM aqueous sulfuric acid solution and allowed to stand at room temperature. A potential of 0.36 Vvs.SCE was applied to working electrode 14. A xenone lamp of 500 W was used as light source 1, a monochromatic light of 600 nm in wavelength was taken out by spectroscope 2 and a step-functional light as shown in FIG. 2(a) was irradiated to the aqueous solution in the electrolytic cell through working electrode 14 by opening shutter 3 for 5 seconds. Thereby, a photocurrent-time response curve as shown in FIG. 2(c) was obtained. There were no changes of concentrations in bulk of Fe (II), Fe (III) and thionine before and after the irradiation of light.

When thionine, semithionine and leucothionine are expressed by Th, S and L, respectively, it is considered that irradiation of light brings about the reactions of the equations (3)–(7).

$$Th + h\nu \rightarrow Th^* \tag{3}$$

$$Th^* + Fe(II) \rightarrow S \cdot + Fe(III) \tag{4}$$

$$S \cdot + Fe(III) \rightarrow Th + Fe(II) \tag{5}$$

$$S \cdot + S \cdot \rightarrow Th + L \tag{6}$$

$$L + Fe(III) \rightarrow S \cdot + Fe(II) \tag{7}$$

It is considered that on the working electrode the following reaction (8) takes place and as a result photocurrent flows therethrough.

$$L \rightarrow Th + 2e \tag{8}$$

This photocurrent i is shown by the following formula (9) during the time of irradiation which was found to substantially correspond to measured value.

$$i = \frac{nFAD^{\frac{1}{2}}\beta}{K^{\frac{1}{2}}} \, erf(K^{\frac{1}{2}} t^{\frac{1}{2}}) \tag{9}$$

That is, it became clear that apparent first order reaction rate constant K, quantum efficiency, etc. can be obtained by drawing a photocurrent-time response curve. Here, the states of the curve of from t$_1$ to t$_2$ and that of after t$_2$ in FIG. 2(c) are observed. In the above formula, $\beta = \ln 10 \cdot \Phi_1 \Phi_2 \epsilon a^\circ I^\circ$, n is the number of redox electrons, F is Faraday's constant, A is surface area of the electrode, D is a diffusion constant, $\Phi_1$ is a quantum efficiency of semithionine production, $\Phi_2$ is a partial ratio of semithionine which produces leucothionine, $\epsilon$ is a molar absorption coefficient of thionine, a$^\circ$ is a bulk concentration of thionine and I$^\circ$ is a quantity of incident light.

The formula (9) shows that when photocurrent value is measured at a constant light quantity, I$_o$ and irradiation time, concentration of thionine can be measured from the photocurrent value.

Next, wave form of light irradiated will be explained with reference to FIG. 3. A step-functional light of constant in intensity during the time from t$_1$ to t$_2$ as of FIG. 3(a) is suitable. When intensity changes during the time of from t$_1$ to t$_3$ and from t$_4$ to t$_2$ as shown in FIG. 3(b), it is difficult to analyze current-time response curve. The analysis is difficult also when the intensity changes during from t$_1$ to t$_2$ as in FIG. 3(c).

Since light is irradiated and current is measured in the example shown in FIG. 1 mentioned above, effects caused by stray lights or interference are smaller than when light absorption is measured. Furthermore, when sample solutions contain substances which react by irradiation of light while they are in electric field, analysis of mechanism of photochemical reaction or measurement of reaction rate constant can be performed by observing transitional phenomena of the reaction. Moreover, even if the sample solution is low in light transmission, since light is irradiated to the sample solution after it just passes through the working electrode, such a light as has been absorbed and decayed is not used and thus efficient photochemical reaction can be brought about. Measurement with high current values becomes possible by measuring the current values within the period of light irradiation and thus measurement of components at high sensitivity becomes possible.

Figure 4:
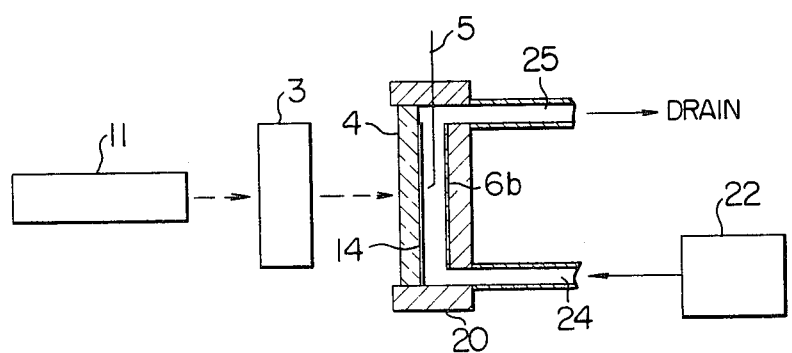
FIG. 4 is a rough block diagram which shows another embodiment of this invention.

FIG. 4 shows a rough block diagram of another example of this invention. In this example, an electrochemical detector is used as a detector of a liquid chromatograph. Electrolytic cell 20 of flow type has an inlet 24 and outlet 25 for the liquid. Light transmitting window 4 constitutes a part of the cell wall as in the example of FIG. 1 and has working electrode 14 on its inner surface. The reference number 6b indicates an auxiliary electrode. The effluent from a separating column of liquid chromatograph 22 is allowed to flow into electrolytic cell 20 from inlet 24. The light from laser light source 11 is adjusted to become step-functional light by light switch 3 and repeatedly irradiated to electrolytic cell 20 as light pulses having a given period. To the solution passing through electrolytic cell 20 is irradiated the light which has been transmitted through working electrode 14. Therefore, photocurrents corresponding to the amounts of separated components which flow in the form of bands are obtained. The resultant photocurrents are amplified synchronously with opening and shutting of light switch. Quantitative analysis of each component is conducted based on the previously obtained calibration curve.

According to the example of FIG. 4, there is obtained the effect that many samples can be successively and efficiently measured besides the effect obtained by the example of FIG. 1.

What is claimed is:

1. A method of electrochemical measurement utilizing photochemical reaction which includes using an electrolytic cell having a light transmissible wall, a light transmissible working electrode being provided on inner surface of said light transmissible wall; irradiating a monochromatic light to a sample solution in said electrolytic cell through said working electrode by directing the monochromatic light to the electrolytic cell; and measuring changes in current which are caused by photochemical reaction in said electrolytic cell brought about by said irradiation of light.

2. A method of electrochemical measurement according to claim 1, wherein the sample solution is allowed to flow through said electrolytic cell and the monochromatic light is intermittently irradiated to said electrolytic cell.

3. A method of electrochemical measurement according to claim 1, wherein said light is of constant intensity when irradiating the electrolytic cell.

4. A method of electrochemical measurement according to claim 1, wherein the measuring is performed during the period of light irradiation.

5. A method of electrochemical measurement according to claim 1, wherein the directing of the monochromatic light to the electrolytic cell is performed by passing said light into the cell to the sample solution through the light transmissible wall.

6. A method of electrochemical measurement according to claim 1, wherein the monochromatic light is intermittently irradiated to said electrolytic cell.

7. An apparatus for electrochemical measurement utilizing photochemical reaction which comprises an electrolytic cell, at least a part of a wall of which is of a light transmissible material and into which cell a sample containing substances capable of bringing about photochemical reaction is introduced; a light transmissible working electrode provided on inner surface of said light transmissible material forming said at least a part of a wall; an auxiliary electrode provided in said electrolytic cell; a means for irradiating a monochromatic light in a step-functional state to said electrolytic cell; and a means for detecting changes in current which are caused by photochemical reaction brought about by the irradiation of light which has been transmitted through said working electrode.

8. An apparatus for electrochemical measurement according to claim 7, wherein the working electrode comprises a metal film vapor deposited on the inner surface of the light transmissible material forming said at least part of a wall.

9. An apparatus for electrochemical measurement according to claim 7, wherein a light switching means capable of instantaneously opening and shutting the light path of the monochromatic light from a monochromatic light emitting means is provided and a light in a step-functional state is obtained by working of said light switching means.

10. An apparatus for electrochemical measurement according to claim 7, wherein the working electrode comprises a two-layer film of chromium, as the first layer, deposited on the light transmissible material and gold deposited on the chromium layer.

11. An apparatus for electrochemical measurement according to claim 7, wherein the working electrode is a layer of tin oxide or indium oxide deposited on the light transmissible material.

12. An apparatus for electrochemical measurement according to claim 7, wherein said electrolytic cell is of a flow type through which the sample solution is allowed to flow.

13. An apparatus for electrochemical measurement according to claim 7, wherein said means for irradiating is positioned to irradiate light to the sample in the electrolytic cell by passing light into the cell through the light transmissible material forming said at least a part of a wall.

* * * * *